United States Patent [19]

West, Jr.

[11] Patent Number: 5,904,681
[45] Date of Patent: May 18, 1999

[54] ENDOSCOPIC SURGICAL INSTRUMENT WITH ABILITY TO SELECTIVELY REMOVE DIFFERENT TISSUE WITH MECHANICAL AND ELECTRICAL ENERGY

[75] Inventor: Hugh S. West, Jr., 1373 Harvard Ave., Salt Lake City, Utah 84105

[73] Assignee: Hugh S. West, Jr., Salt Lake City, Utah

[21] Appl. No.: 08/797,429

[22] Filed: Feb. 10, 1997

[51] Int. Cl.$^6$ .................................................. A61B 17/32
[52] U.S. Cl. ................................ 606/41; 606/46; 606/48; 606/50; 606/170; 604/22
[58] Field of Search .................................. 606/34, 41, 45, 606/46, 48–50, 170, 179, 180; 604/22

[56] References Cited

U.S. PATENT DOCUMENTS

| | | |
|---|---|---|
| 3,828,780 | 8/1974 | Morrison, Jr. . |
| 3,945,375 | 3/1976 | Banko . |
| 4,815,462 | 3/1989 | Clark . |
| 4,850,354 | 7/1989 | McGurk-Burleson et al. . |
| 4,998,933 | 3/1991 | Eggers et al. . |
| 5,178,620 | 1/1993 | Eggers et al. . |
| 5,364,395 | 11/1994 | West, Jr. . |
| 5,366,443 | 11/1994 | Eggers et al. . |
| 5,419,767 | 5/1995 | Eggers et al. . |
| 5,472,441 | 12/1995 | Edwards et al. ........................... 606/49 |
| 5,527,331 | 6/1996 | Kresch et al. ............................. 606/45 |
| 5,575,810 | 11/1996 | Swanson et al. ......................... 607/122 |

*Primary Examiner*—Jeffrey R. Jastrzab
*Assistant Examiner*—David M. Ruddy
*Attorney, Agent, or Firm*—Workman, Nydegger & Seeley; John M. Guynn

[57] ABSTRACT

Surgical instruments which have multiple functions used in performing endoscopic surgeries, including arthroscopic surgery. The surgical instrument includes a mechanical cutting portion, such as a rotary blade or burr, and an electronic cutting and/or cauterizing portion comprising an electronic surgical device which operates in bipolar mode. This solves the problem of having to constantly remove and insert various surgical instruments into the surgery site in order to remove different kinds of tissues and at different rates and in different manners. A rotary burr works best to remove hard tissues, such as bone, while the bipolar device can be used to cut or ablate soft tissues and/or cauterize tissue, including blood vessels. Alternatively, the mechanical cutting portion may include a rotary blade, which works best for removing soft tissues.

23 Claims, 4 Drawing Sheets

ENDOSCOPIC SURGICAL INSTRUMENT WITH ABILITY TO SELECTIVELY REMOVE DIFFERENT TISSUE WITH MECHANICAL AND ELECTRICAL ENERGY

BACKGROUND OF THE INVENTION

1. The Field of the Invention

The present invention relates generally to endoscopic surgical instruments. Specifically, the present invention relates to surgical instruments that can selectively use both mechanical energy and electrical energy to remove tissue of a patient at an internally located surgical site. More specifically, the surgical instruments include a portion that operates in bipolar mode to cut, ablate, or cauterize tissues during an endoscopic procedure.

2. The Relevant Technology

Endoscopy is widely used in order to effect removal of unwanted or damaged tissues from a patient in a manner that is less invasive than completely opening up the tissue and using traditional cutting tools. The result is greatly shortened patient recovery, minimal scarring, reduced cost, elimination of typical pre-operative and post-operative hospital stays, and widespread use to correct a variety of injuries. A particular form of endoscopy, arthroscopy, is widely known and used to operate on joints, such as shoulders or knees.

An endoscope allows a doctor to look directly into a surgical site through a first incision, which allows for a minimally invasive procedure useful for both diagnosis and treatment. Typical endoscopes include a magnifying lens and coated glass fibers that beam an intense, cool light into the surgical site. The surgical field is viewed on a video monitor connected to an endoscopic video camera.

While viewing the surgical site in the manner described, the surgeon can perform any necessary repair and reconstruction using a separate surgical instrument inserted through a second incision at the surgical site. The surgical instrument can utilize a variety of mechanical cutting tools, such as rotating blades (straight or serrated) or burrs. Such mechanical cutting tools, or shavers, are well known in the art and require no further explanation. In general, rotating blades are generally used to excise unwanted or damaged soft tissues, while burrs are used on harder tissues such as bone.

The foregoing mechanical cutting or shaving tools are very useful for cutting and removing unwanted tissues in a less invasive and destructive manner compared to other surgical tools because they can be inserted through relatively small incisions that provide access to the surgical site. In this manner, they allow for a far less invasive and destructive surgery compared to typical surgical devices, which typically require far larger incisions and involve far higher destruction of perfectly healthy and normal tissues as the surgeon attempts to access the surgical site.

In addition to the aforementioned mechanical cutting tools, electronically powered cutting and cauterizing tools have been developed that also allow for less invasive surgical techniques than previous surgical tools. Such devices are known in the medical industry as either "monopolar" and "bipolar" devices. Both monopolar and bipolar devices have historically included a single positive, or lead, electrode that can be appropriately directed or situated to effect the cutting of soft tissues or cautery of bleeding vessels and tissues. Such devices have been referred to by some as "hot knives".

Whether a surgical electrode device is "monopolar" or "bipolar" depends on the location of the negative, or return, electrode. In a "monopolar" device, the return electrode is remotely connected somewhere else on the patient relative to the lead electrode. In this manner, the electrical current that is generated as a result of the application of a voltage potential to the lead electrode passes from the lead electrode through the tissue or blood vessel being cut or cauterized, through the intervening tissue of the patient's body, and to a grounding pad located remotely on the patient's body. Thus, a substantial portion of the pathway through which the current passes is the intervening tissue of the patient's body. However, since the current can be diffused over a relatively large area of tissue relative to the focused area where energy is applied by the lead electrode, the patient is not normally adversely affected by the passage of current through his or her body.

On the other hand, the return electrode in a "bipolar" device is located in the near vicinity of the lead electrode on the same surgical instrument. Typically, bipolar devices resemble tweezer-like structures comprising dual lead and return electrodes, although such devices are generally not used in endoscopic procedures. In practice, bipolar devices having a single positive lead have been used in a manner similar to monopolar devices in order to cauterize tissues.

Bipolar electrodes having multiple leads or positive electrodes have recently been developed that can be used to ablate or cauterize tissues soft tissues. Examples of multiple lead bipolar devices are set forth in U.S. Pat. Nos. 4,998,933; 5,178,620; 5,366,443; and 5,419,767, all to Eggers et al. (hereinafter the "Eggers et al. patents"). In general, multiple lead bipolar devices works by passing varying levels of high frequency electrical energy through individually powered multiple leads and into the tissue to be ablated or cauterized. The current that is generated as a result of applying voltage potentials to the multiple leads completes a circuit by returning to a single return, or common, electrode located on the same surgical instrument and connected to a ground by means of an insulated ground wire.

Due to its ability to destroy soft tissues by ablation, the multiple electrode bipolar devices can be used in a manner similar to mechanical cutters for removing unwanted or target tissues during an endoscopic procedure. However, multiple electrode bipolar devices have been found to be less efficient compared to single electrode bipolar devices in cauterizing tissues. Moreover, both monopolar and bipolar devices are limited by their inability to remove bone and the fact that they are less efficient and relatively slow in cutting or removing soft tissues compared to mechanical cutting tools. Nevertheless, they have found some use in a variety of surgical applications, as understood by those of ordinary skill in the art. For the ablative removal of relatively small amounts of soft tissues, multiple lead bipolar devices have proven useful.

Because both mechanical endoscopic surgical tools, such as rotary blades or burrs, and electronic devices, such as monopolar and bipolar devices, can be inserted through relatively small incisions to the surgical site, both mechanical and electrical devices can be used in succession and inserted through the same incision as the need arises to carry out a variety of desired surgical functions. For example, if the view of the surgical site has become obscured by excessive bleeding, sometimes caused by the mechanical cutting or shaving device, the surgeon can remove the mechanical cutting device from the incision and then insert through the same incision an electronic device in order to cauterize the bleeding tissue and blood vessels By removing the unwanted blood by known methods, vision to the surgical site can be restored or maintained.

Similarly, the surgeon might wish to utilize the various cutting or ablating features of the aforementioned monopolar and bipolar devices as needed as the surgery progresses in order to fine-tune the surgical process and remove the desired amount of damaged tissue in a desired manner.

While the various mechanical and electronic tools described above are useful in performing a variety of surgical functions, such as cutting, shaving, cautery, and ablating, their use requires the constant removal and insertion of at least two different tools, and possibly more, through the same incision. For example, if the surgeon wished to remove both hard and soft tissues from the same surgical site and/or cauterize and/or ablate tissues, the surgeon would have to insert and withdraw different surgical tools specially designed for performing the foregoing surgical functions. The constant insertion and removal of different surgical tools through the incision to the surgical site both complicates and lengthens the surgical procedure compared to if a single surgical instrument could be used.

In view of the foregoing, it would be an advancement in the art of the endoscopic surgery to provide a single surgical instrument that could simultaneously provide different surgical functions in order to eliminate or reduce the need to remove and insert different surgical instruments through the same incision.

It would be a further advancement in the art to provide a single surgical instrument that could be used to remove both hard and soft tissues at the surgical site as needed.

It would be an additional advancement in the art if the ability to remove both soft and hard tissues by a single surgical instrument could be performed selectively such that the means for removing hard tissue could be activated independently of the means for removing soft tissue.

It would yet be a further advancement in the art of surgery to provide a single surgical instrument that had the ability to more efficiently cauterize ruptured blood vessels or bleeding tissue in addition to removing either hard or soft tissues at the surgical site.

It would be an additional advancement in the art if the means for cauterizing tissue could be activated independently of either of the means for removing damaged or unwanted hard or soft tissues.

It would be a further advancement in the art of surgery to provide a single surgical instrument that provided the surgeon with the ability to electronically ablate soft tissues in addition to removing either hard or soft tissues by mechanical cutting or shaving.

It would be an additional advancement in the art if the means for ablating soft tissues could be activated independently of the means for removing damaged or unwanted hard or soft tissues by mechanical cutting or shaving.

Such multi-functional surgical instruments are described and claimed herein.

SUMMARY AND OBJECTS OF THE INVENTION

The present invention relates to surgical instruments that include both a mechanical cutting tool and an electronically powered surgical device that operates in bipolar mode. This allows for the ability to cut and/or ablate and/or cauterize different kinds of tissues at different rates or in different ways without having to withdraw and insert different surgical tools.

In a preferred embodiment of the present invention, the surgical instrument will include a rotary burr that can be used to surgically remove bone or other hard tissues during endoscopy surgery, typically arthroscopic surgery. In addition to the rotary burr, the surgical instrument will include an electronically powered surgical device that operates in bipolar mode for, e.g., ablating unwanted or damaged soft tissues in the vicinity of the bone or other hard tissues at the surgery site. The bipolar surgical device can include a single lead electrode, or include a plurality of lead electrodes. An example of bipolar devices having a plurality of lead electrodes is described in the Eggers et al. patents.

Because it is advantageous for the rotary burr and bipolar device to be operated independently, the surgical instrument will preferably include a plurality of switching mechanisms for selectively activating the burr and bipolar electrode as needed. In this manner, the surgeon can remove both hard tissues, such as bone, and soft tissues, such as surrounding flesh, using a single medical instrument. This eliminates the need to remove the rotary burr and insert a different mechanical cutting tool or bipolar electrode for removing soft tissues, removing the second instrument, and then reinserting the rotary burr to further clear away the hard tissues. Not only does this simplify the operation, but it allows the surgeon to maintain the cutting tools in the location where they are needed and reduces the incidence of enhanced bleeding that might occur because of the constant insertion and withdrawal of different surgical tools through the incision to the wound site.

In addition to ablating unwanted tissues, the bipolar device can instead be used to cauterize bleeding tissues or blood vessels. Typically, a multiple prong bipolar device is preferable for ablating tissues, while a single lead electrode is preferable for cauterizing tissues. Nevertheless, it should be possible to switch between ablation and cautery using a multiple prong device by altering the energy input to the lead electrodes. After ablating tissue it might be desirable to cauterize bleeding tissues at the surgical site in order to maintain a clear view of the surgical site, which can become obscured by excessive bleeding.

In yet another embodiment of the present invention, a rotating blade, such as those used to mechanically remove soft tissues, could be combined in a single instrument with the bipolar surgical tool to provide an alternative surgical tool that would provide the surgeon with alternative tissue removal capabilities. Whereas a rotating blade is generally used to cut soft tissues, the bipolar electrode could be used to ablate soft tissues and/or cauterize bleeding tissue or blood vessels in a single surgical device without having to withdraw the rotary blade in order to insert a separate bipolar instrument. Eliminating one or more additional surgical devices to provide the desired multiplicity of surgical functions will have the aforementioned benefit of allowing for a less complicated and more streamlined operation.

In embodiment, the lead electrode in the bipolar device will preferably include a single enlarged electrode that is preferably located at or near the tip of the surgical device in the vicinity of the mechanical cutting tool. In this manner, the mechanical and electronic surgical portions can be used to remove and cauterize tissues as needed in the same general area of the surgical site. Of course, one of ordinary skill in the art will appreciate that the lead electrode can be located at any desired location that would provide the desired function demanded by the particular surgical procedure in question.

The negative, or return, electrode will typically be located within the surgical instrument in the vicinity of the positive electrode in order to provide efficient bipolar operation. In this manner, the surgical device is said to be "bipolar" due to the location of the positive electrode and return electrode in the same general vicinity within the surgical device. Bipolar devices that had a single lead or positive electrode are best suited for cauterizing tissues.

In yet another embodiment of the present invention, the bipolar portion of the surgical device may include a plurality of positive or lead electrodes that are independently powered in order to input varying amounts of electrical energy across the of positive electrodes. This type of electrode array is described more fully in the Eggers et al. patents identified above. For purposes of disclosing both the design and operation of multiple electrode devices, the Eggers et al. patent are incorporated herein by specific reference. Bipolar devices that have multiple leads or positive electrodes are best suited for ablating soft tissues.

Although the present invention contemplates a surgical instrument having a mechanical cutting tool in combination with a bipolar device for ablating and/or cauterizing tissues, one of ordinary skill in the art would appreciate that there might be other combinations of different surgical tools that might prove useful. For example, one could envision the inclusion of an electronic device having multiple leads or positive electrodes which operates in monopolar mode with a remote common or return electrode located remotely on the patient's body. For example, U.S. Pat. No. 5,364,395 to West, Jr. generally discloses a surgical instrument that includes a monopolar electronic device.

In light the foregoing, it is an object of the present invention to provide a single surgical instrument that simultaneously provides different surgical functions in order to eliminate or reduce the need to remove and insert different surgical instruments through the same incision.

It is a further object and feature of the present invention to provide a single surgical instrument that can be used to remove both hard and soft tissues at the surgical site as needed.

Specifically, it is an object of the present invention that the ability to remove both soft and hard tissues by a single surgical instrument can be performed selectively such that the means for removing hard tissue can be activated independently of the means for removing soft tissue.

It is yet an object of the present invention to provide a single surgical instrument that has the ability to more efficiently cauterize ruptured blood vessels or bleeding tissue in addition to removing damaged or unwanted hard or soft tissues at the surgical site.

Specifically, it is an object and feature of the present invention that the means for cauterizing tissue can be activated independently of the means for removing damaged or unwanted hard or soft tissues.

It is a further object and feature of the present invention to provide a single surgical instrument that provides the surgeon with the ability to electronically ablate soft tissues in addition to removing either hard or soft tissues by mechanical cutting or shaving.

It is an object of the present invention that the means for ablating soft tissues can be activated independently of the means for removing damaged or unwanted hard or soft tissues by mechanical cutting or shaving.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention encompasses surgical instruments that allow for a variety of different surgical operations or functions to be performed using a single surgical instrument. The surgical instrument includes both a mechanical cutting tool, such as a serrated blade or a rotating burr, and an electronic surgical device that operates in bipolar mode in order to ablate soft tissues in and around the area where the mechanical cutting tool is used and/or to cauterize bleeding tissue.

The surgical instruments of the present invention can be used in any form of endoscopy. In the case of arthroscopic surgery in which bone is removed, a preferred embodiment of the present invention will include a rotary burr for removing bone in combination with a bipolar device for cutting or ablating soft tissues and/or for cauterizing blood vessels. Nevertheless, it should be understood that other forms of endoscopy not involving bones or joints can be performed using the surgical instruments of the present invention. In cases where it will be desired to remove soft tissue, the preferred mechanical cutting tool will include a rotary blade rather than a burr. The surgical instruments of the present invention can be used for, e.g., surgery of the facial area, internal organs, to remove cancerous tissues, and for joint reparation. The foregoing list is illustrative, not limiting.

In order to more specifically teach how to manufacture certain embodiments of the present invention, reference will be made to the drawings. It should be understood that the invention relates to the combination of a mechanical cutting tool together with a surgical device capable of bipolar operation within a single surgical instrument in order to eliminate or reduce the need to withdraw and insert various surgical instruments through the incision to the wound site in order to perform a variety of desired surgical functions. The present invention is not limited to the particular embodiments depicted in the drawings, although they represent preferred embodiments as will be discussed.

Figure 1:
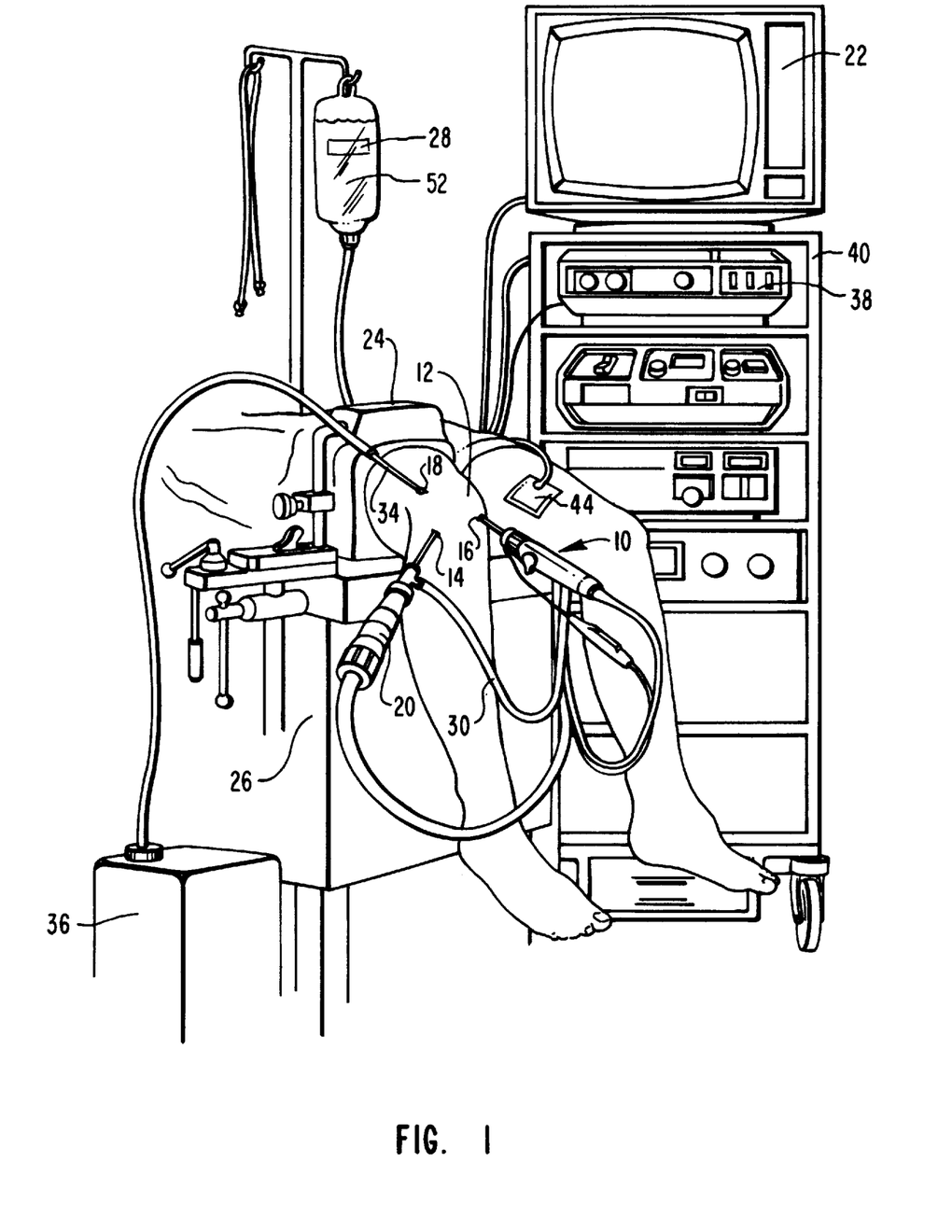
FIG. 1 is a perspective view of an operating room where surgery is being conducted on the knee of a patient.

FIG. 1 is a perspective view of an operating room where arthroscopic surgery is being conducted on the knee of a patient using a surgical instrument 10 adapted for arthroscopic surgery and incorporating the teachings of the present invention. A knee 12 is shown on an operating table 26 with an arthroscope portal 14, an instrument portal 16, and a suction portal 18 created therein, which all lead to and communicate with the surgical site. It is contemplated that the surgical instruments of the present invention are used in connection with an arthroscope 20, which is inserted through the arthroscope portal 14 in order to provide visual communication with the surgical site. In order to restrain the knee 12 from unwanted movements during the surgical procedure, a brace 24 may secure the knee 12 to the operating table 26.

As used herein, the term "surgical site" includes any location in the body of a patient at which surgery is performed. Thus, although knees and shoulders have been discussed as likely surgical sites for arthroscopy surgery, the term "surgical sites" as used in this application may include any location in the body of a patient where surgery may be performed. Hence, although it is contemplated that the present invention will be used with an arthroscope, the present invention is not limited solely to that procedure, though the present embodiment is particularly adapted for arthroscopic surgery. They are also well adapted for performing less invasive facial surgeries.

When using an arthroscope 20, the individual performing the surgical procedure is capable of viewing the surgical site within the knee 12 on a monitor 22 that is attached to the arthroscope 20. In order to maintain clarity of view and to remove unwanted blood, a sterile fluid 52 contained in a bag 28 is passed through a sterile fluid tube 30 and into the surgical site through passageways built into the arthroscope 20. A suction tube 34 is inserted through the suction portal 18 in communication with the surgical site in order to drain excess fluid from the surgical site, which is then deposited in a waste fluid container 36.

In order to perform the surgical procedure, the surgical instrument 10 is inserted through the instrument portal 16 which communicates with the surgical site. The nature and extent of the tissue removal is determined after viewing the surgical site on the monitor 22 by means of the arthroscope 20. As shown in FIG. 1, the surgical instrument 10 is coupled to a power source 38 that resides on a stand 40. The surgical instrument 10 may also be connected to a vacuum source in order to remove waste fluids into a container similar to the waste fluid container 36.

In the event that it is desired to ground the patient, such as where the surgeon wishes to use a monopolar device instead of or in conjunction with the surgical device of the present invention, a grounding patch 44 may be positioned on the patient's leg in order to complete an electrical circuit with a power source (not shown). Other monitoring instruments positioned on the stand 40 are also depicted in FIG. 1, which may have some use during the surgical procedure.

Figure 2:
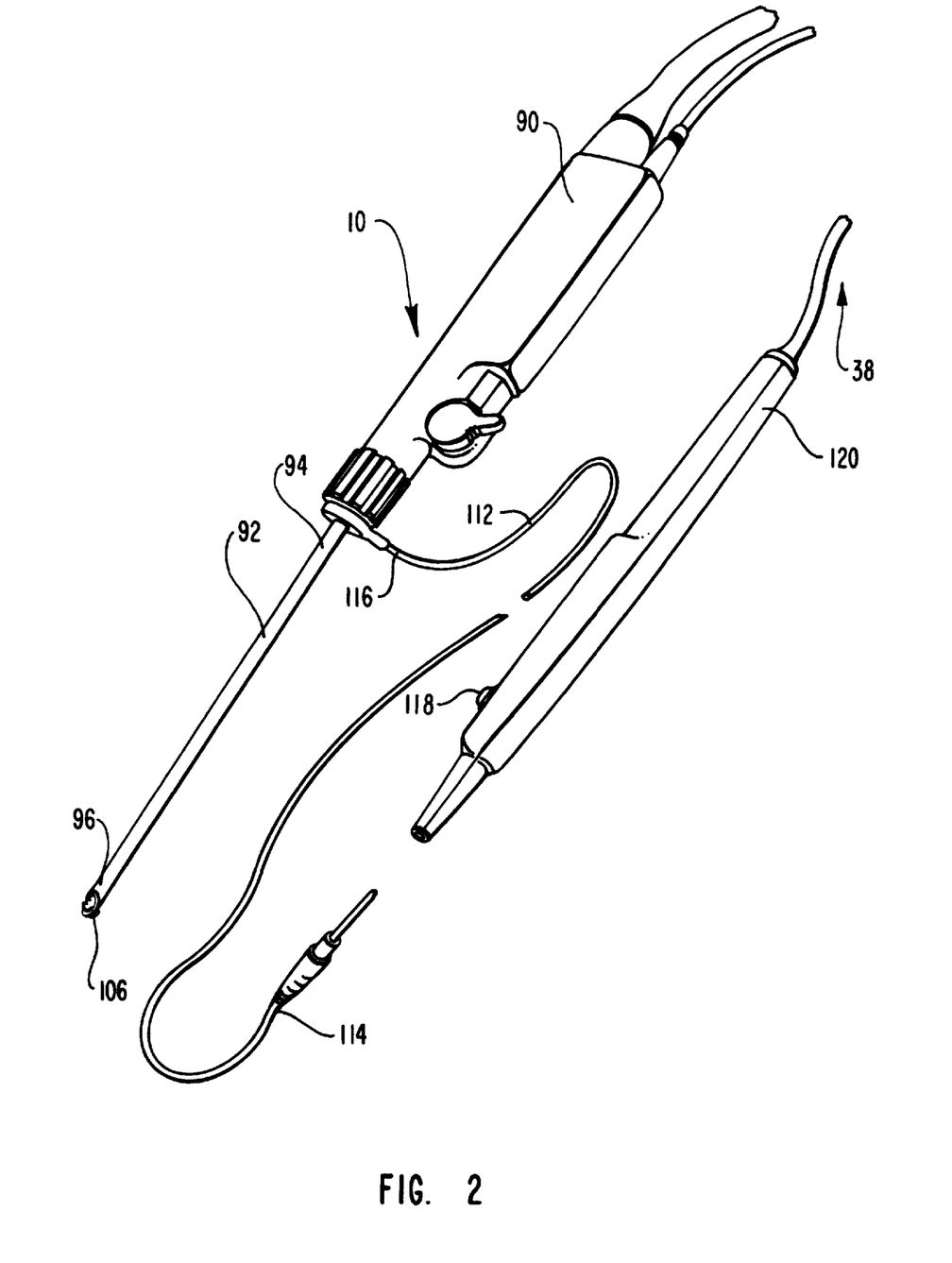
FIG. 2 is a perspective view of the inventive instrument.

As depicted in FIG. 2, the presently preferred embodiment of the surgical instrument 10 is provided with both a mechanical cutting or shaving tool, such as a rotary blade or burr, and a bipolar electrode for removing both hard and soft tissues. The surgical instrument 10 includes a handle 90 and a probe 92 protruding therefrom that has a proximal end 94 and a distal end 96. The probe 92 is hollow and includes therein a rotatable shaft connected to a mechanical cutting tool at the distal end of the probe 92. The rotatable shaft is connected to a motor, which can be turned on and off when desired in order to rotate the mechanical cutting tool and effect excision of tissue. The specific features of the distal end 96 of the probe 92 will be described hereinbelow.

In addition to the mechanical cutting tool shown generally at distal end 96 of the probe 92, an electronic surgical device 106 that operates in bipolar mode is also disposed at the distal end 96. The means for energizing the electronic surgical device 106 comprises a cable 112 having a first end 114 that communicates with a power generating source (not shown) and a second end 116 that is attached to the surgical instrument 10. The first end 114 is coupled to the power generating source by means of cable 38, which is connected to a switching body 120, which includes a switch 118. This allows the surgeon to supply power to the bipolar device when desired.

Figure 3:
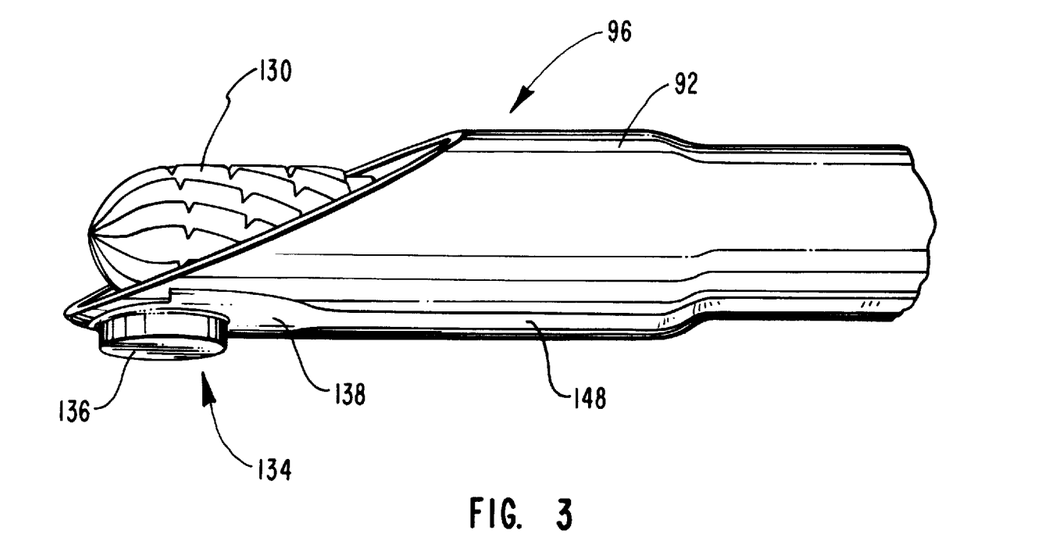
FIG. 3 is a perspective view of the distal end of a preferred embodiment of the instrument incorporating a rotary burr as the mechanical cutting means and a single-lead bipolar device disposed near the tip of the instrument.
Figure 4:
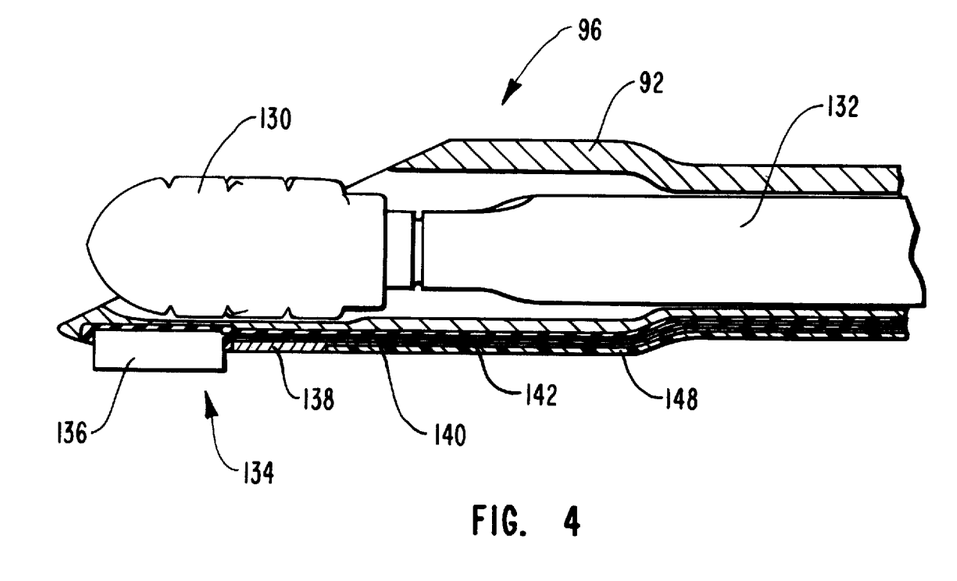
FIG. 4 is a longitudinal cross-sectional view of the surgical instrument depicted in FIG. 3.

FIG. 3 is an enlarged detailed view of a preferred embodiment of the inventive surgical instrument, more particularly of the distal end 96 of the surgical instrument 10. FIG. 4 is a cross-sectional view of the surgical instrument depicted in FIG. 3. FIGS. 3 and 4 depict a surgical instrument having mechanical cutting means and a bipolar electronic device. The mechanical cutting means includes as the mechanical cutting tool a rotary burr 130 that is connected to a rotatable shaft 132, which is longitudinally disposed within the hollow probe 92. The rotatable shaft 132 is connected to a motor (not shown) which drives the shaft 132, which in turn causes the burr 130 to rotate when needed.

The hollow shaft 92 can be made of any material that will have sufficient strength and durability so that it may withstand the forces associated with the surgical operation for which the instrument is intended. In a preferred embodiment, the hollow probe 92 will simply comprise a metal. If it comprises a metal, the hollow shaft 92 can serve as the common electrode if desired and in any event will preferably be insulated electronically from positive lead wire connected to the positive terminal. In the embodiment shown, both the positive lead wire and grounding wire are electronically insulated from the hollow shaft 92 by means of an insulating sheath 148, which is embedded within a groove formed on the under side of the hollow probe 92. Alternatively, the hollow probe 92 may comprise a hard plastic material or a metal coated with a plastic material for insulation.

The distal end 96 of the probe 92 also includes a bipolar device assembly 134, which includes at least one positive electrode 136 and a common electrode 138 located nearby. The positive electrode 136 and common electrode 138 are electronically insulated from each other such that they do not create a closed circuit, except to the extent that there is a conductive fluid (such as blood) or tissue in the vicinity of the bipolar electrode, which will complete the circuit when the bipolar device is energized.

The positive electrode 136 is connected electronically to a power generating source (not shown) by means of a positive lead wire 140. The common electrode 138 is connected to a ground by means of a common return wire 142, which is electronically insulated from the positive lead wire 140 and from the hollow probe 92 by means of the insulating sheath 148 in this embodiment. The power generating means (not shown) includes switching means for energizing the bipolar device 134 when desired and also for regulating the power that is applied thereto. In that way, the power level to the bipolar device 134 can be regulated in order to effect cutting, ablation, or cauterization of bleeding tissues. In general, bipolar devices having a single positive electrode work best for cautery, while multiple lead bipolar devices work best for ablating soft tissues.

Figure 5:
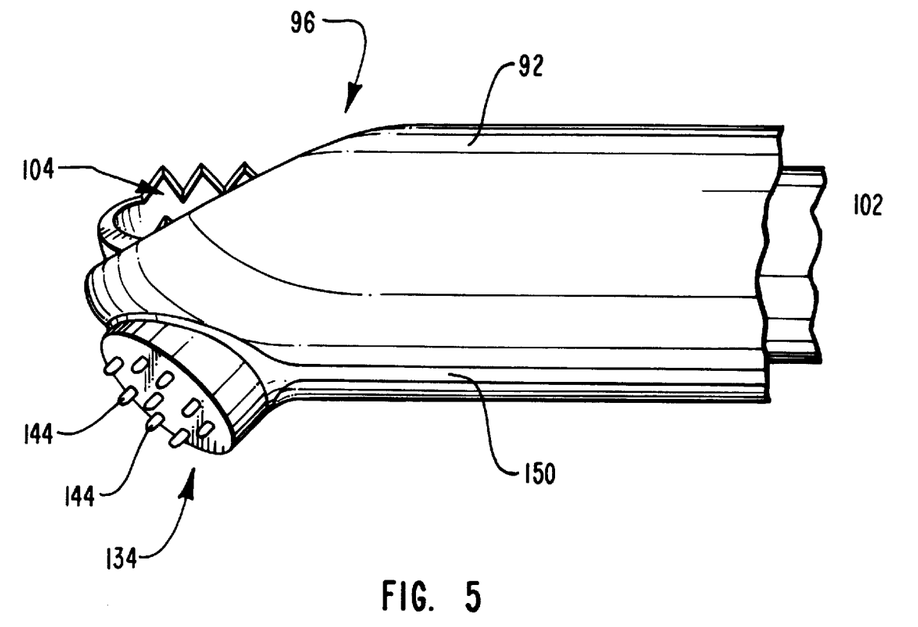
FIG. 5 is a perspective view of the distal end of an embodiment of the present invention using a serrated blade as the mechanical cutting tool and a multi-lead bipolar device disposed near the tip of the instrument.
Figure 6:
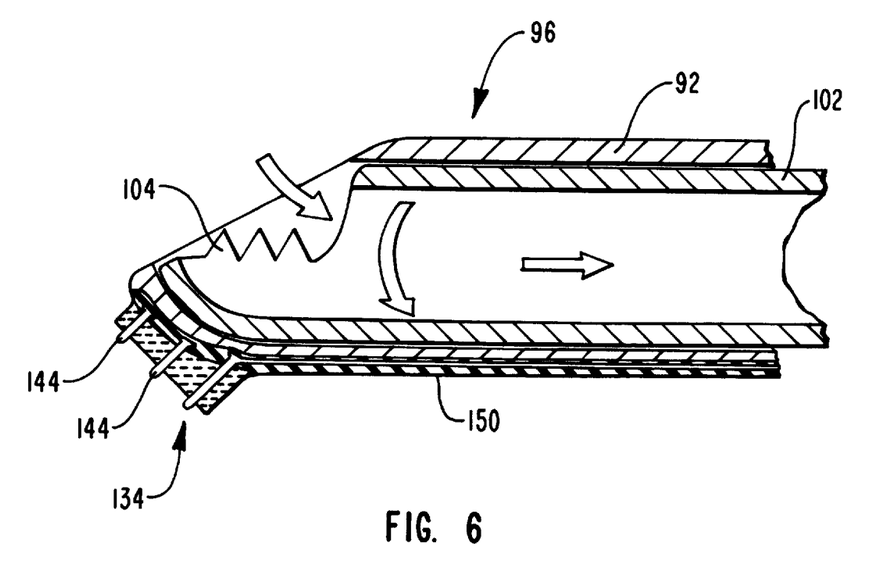
FIG. 6 is a longitudinal cross-sectional view of the instrument of FIG. 5.

FIG. 5 depicts an alternative embodiment of the present invention, in which the mechanical cutting tool comprises a serrated blade 104 connected to a shaft 102 longitudinally disposed within the hollow probe 92. In addition, the bipolar device 134 includes a plurality of positive electrodes 144. The common or return electrode is shown to comprise the hollow probe 92, which comprises a metallic substance and which is electronically interfaced with the grounding means (not shown). In addition, the hollow probe 92 is shown to be electronically insulated from the lead wires that supply power to the positive electrodes 144 by means of insulating sheath 150, which is embedded within a groove formed on the under side of the hollow probe 92.

The rotatable drive shaft 102 is connected to a motor (not shown), which can be selectively activated in order to provide cutting by means of the serrated blade 104 as desired. In addition, the bipolar device 134 can be energized when needed by means of the power generating means (not shown), which may include means for altering the level of energy input to the different positive electrodes 144 as desired. In this way, the level of heating or tissue ablation can be regulated and directed to particular areas within the bipolar device 134 as needed.

The present invention contemplates a surgical instrument having a mechanical cutting tool in combination with a bipolar device for ablating and/or cauterizing tissues. However, one of ordinary skill in the art would appreciate that there might be other combinations of surgical tools that might prove useful. One could envision the combination of a multiple lead monopolar device for cutting or cauterizing coupled with a mechanical cutting tool, such as a burr or blade.

In view of the foregoing discussion, the present invention provides a single surgical instrument that simultaneously provides different surgical functions in order to eliminate or reduce the need to remove and insert different surgical instruments through the same incision to access the wound site.

The present invention further provides a single surgical instrument that can be used to remove both hard and soft tissues at the surgical site as needed.

Specifically, the ability to remove both hard and soft tissues by the single surgical instrument can be performed selectively such that the means for removing hard tissue can be activated independently of the means for removing soft tissue.

The present invention also provides a single surgical instrument that has the ability to cauterize ruptured blood vessels or bleeding tissue in addition to removing damaged or unwanted hard or soft tissues at the surgical site.

Specifically, the means for cauterizing tissue can be activated independently of the means for removing damaged or unwanted hard or soft tissues.

The present invention further provides a single surgical instrument that provides the surgeon with the ability to electronically ablate soft tissues in addition to removing either hard or soft tissues by mechanical cutting or shaving.

Specifically, the means for ablating soft tissues can be activated of the means for removing damaged or unwanted hard and soft tissues by mechanical cutting or shaving.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for performing a plurality of surgical operations on a patient at a desired surgical site, the method comprising the steps of:
    (a) forming an access passageway from the exterior of the body of the patient to the surgical site;
    (b) providing a surgical instrument comprising:
        (i) a handle;
        (ii) an elongate hollow probe having a proximal end and a distal end and being attached to the handle at the proximal end;
        (iii) cutting means for mechanically cutting tissue, the cutting means including a rotatable cutting tool disposed at the distal end of the hollow probe and a rotatable drive shaft longitudinally disposed within the hollow probe and connected to the cutting tool, the drive shaft being able to rotate the cutting tool in order to sever tissue adjacent to the cutting tool;
        (iv) an electronic surgical device that operates in bipolar mode disposed at the distal end of the probe and including at least one positive electrode disposed at the distal end of the probe for providing a high frequency voltage and a common electrode separate from the positive electrode and also disposed at the distal of the probe that communicates with a ground for completing a circuit with the positive electrode during bipolar operation, wherein the electronic surgical device is can able of ablating tissue; and
        (v) power generating means for selectively providing the high frequency voltage to the positive electrode;
    (c) insert in the elongate hollow probe through the access passageway in order that the cutting means and the electronic surgical device are located at the surgical site;
    (d) excising a desired amount of tissue by means of the cutting means for mechanically cutting tissue; and
    (e) performing a desired surgical function using the electronic surgical device without completely withdrawing the surgical instrument from the access passageway.

2. A method as defined in claim 1, wherein the desired surgical function performed in step (d) comprises cutting or ablating tissue.

3. A method as defined in claim 1, wherein the desired surgical function performed in step (d) comprises cauterizing bleeding tissue.

4. A method as defined in claim 1, where the cutting tool of the surgical instrument comprises a burr or a blade.

5. A method as defined in claim 1, further including the step of vacuuming waste fluids from the surgical site by means of the surgical instrument.

6. A surgical instrument used in endoscopic surgery comprising:
    (a) a handle;
    (b) an elongate hollow probe having a proximal end and a distal end and being attached to the handle at the proximal end;
    (c) cutting means for mechanically cutting tissue, the cutting means including a rotatable cutting tool disposed at the distal end of the hollow probe and a rotatable drive shaft longitudinally disposed within the hollow probe and connected to the cutting tool, tie drive shaft being able to rotate the cutting tool in order to sever tissue adjacent to the cutting tool;
    (d) an electronic surgical device that operates in bipolar mode disposed at the distal end of the probe the electronic surgical device including at least one positive electrode disposed at the distal end of the probe for providing a high frequency voltage and a common electrode separate from the positive electrode and also disposed at the distal of the probe that communicates with a ground for completing a circuit with the positive electrode during bipolar operation, wherein the electronic surgical device is capable of ablating tissue; and (e) power generating means for selectively providing the high frequency voltage to the positive electrode.

7. A surgical instrument as defined in claim 1, wherein the electronic surgical device is further capable of cutting soft tissues.

8. A surgical instrument as defined in claim 6, wherein the electronic surgical device is further capable of cauterizing tissues, including blood vessels.

9. A surgical instrument as defined in claim 6, wherein the rotatable cutting tool comprises a blade.

10. A surgical instrument as defined in claim 6, wherein the rotatable cutting tool comprises a burr.

11. A surgical instrument as defined in claim 6, wherein the hollow probe is electrically conductive such that it comprises the common electrode and wherein the positive electrode communicates with the power generating means by means of a lead wire that is electrically insulated from the hollow probe.

12. A surgical instrument as defined in claim 6, wherein the hollow probe is electrically insulated from the surgical site and wherein the common electrode is in communication with the ground by means of a common wire located within the surgical instrument.

13. A surgical instrument as defined in claim 6, wherein the electronic surgical device includes a single positive electrode.

14. A surgical instrument as defined in claim 6, wherein the electronic surgical device includes a plurality of positive electrodes.

15. A surgical instrument as defined in claim 14, wherein the positive electrodes individually communicate with the power generating means by means of individual lead wires that connect each of the positive electrodes to the power generating means.

16. A surgical instrument as defined in claim 15, wherein the power generating means is able to selectively provide varying voltages to each of the positive electrodes such that at least one of the positive electrodes can have a different voltage than another of the positive electrodes.

17. A surgical instrument as defined in claim 6, further including means for selectively activating the cutting means such that the cutting means can be activated or deactivated as desired to cut tissue.

18. A surgical instrument as defined in claim 1, wherein the surgical instrument is suitable for connection to a vacuum source in order to remove waste fluids.

19. A surgical instrument which provides a plurality of surgical functions comprising:

(a) a handle;

(b) an elongate hollow probe having a proximal end and a distal end and being attached to the handle at the proximal end;

(c) cutting means for mechanically cutting tissue, the cutting means including a rotatable burr or blade disposed at the distal end of the hollow probe and a rotatable drive shaft longitudinally disposed within the hollow probe and connected to the burr or blade, the drive shaft being able to rotate the burr or blade in order to shave off tissue adjacent to the burr or blade when rotated;

(d) means for selectively activating the cutting means such that the cutting means can be activated or deactivated as desired to cut tissue;

(e) an electronic surgical device that operates in bipolar mode disposed at the distal end of the probe, the electronic surgical device including a single positive electrode disposed at the distal end of the probe for providing a high frequency voltage and a common electrode separate from the positive electrode and also disposed at the distal of the probe that communicates with a ground for completing a circuit with the positive electrode by means of conductive tissue or fluid adjacent to the distal of the probe, wherein the electronic surgical device is capable of ablating tissue; and (f) power generating means for selectively providing the high frequency voltage to the positive electrode.

20. A surgical instrument as defined in claim 19, wherein the electronic surgical device is further capable of cauterizing tissues, including blood vessels.

21. A surgical instrument as defined in claim 19 wherein the surgical instrument is suitable for collection to a vacuum source in order to remove waste fluids.

22. A surgical instrument which provides a plurality of surgical functions comprising:

(a) a handle;

(b) an elongate hollow probe having a proximal end and a distal end and being attached to the handle at the proximal end;

(c) cutting means for mechanically cutting tissue, the cutting means including a rotatable blade or burr disposed at the distal end of the hollow probe and a rotatable drive shaft longitudinally disposed within the hollow probe and connected to the blade or burr, the drive shaft being able to rotate the blade or burr in order to excise tissue adjacent to the blade or burr when rotated;

(d) means for selectively activating the cutting means such that the cutting means can be activated or deactivated as desired to cut tissue;

(e) an electronic surgical device that operates in bipolar mode disposed at the distal end of the probe and including a plurality of positive electrodes disposed at the distal end of the probe for providing a high frequency voltage and a common electrode separate from the positive electrodes, and also disposed at the distal of the probe that communicates with a ground for completing a circuit with the positive electrodes by means of conductive tissue or fluid adjacent to the distal end of the probe, wherein the electronic surgical device is capable of ablating tissue; and (f) power generating means for selectively providing the high frequency voltage to the positive electrode.

23. A surgical instrument as defined in claim 22, wherein the surgical instrument is suitable for connection to a vacuum source in order to remove waste fluids.

* * * * *

UNITED STATES PATENT AND TRADEMARK OFFICE
CERTIFICATE OF CORRECTION

PATENT NO. : 5,904,681

DATED : May 18, 1999

INVENTOR(S) : Hugh S. West, Jr.

It is certified that error appears in the above-identified patent and that said Letters Patent is hereby corrected as shown below:

Col. 2, line 26, after "cauterize" delete "tissues"

Col. 2, line 30, after "devices" change "works" to --work--

Col. 4, line 54, after "In" insert --one--

Col. 5, line 10, after "the" delete "of"

Col. 5, line 13, before "are" change "patent" to --patents--

Col. 9, line 19, after "level of" delete the paragraph break

Col. 10, line 26, after "distal" insert --end--

Col. 10, line 29, after "device is" change "can able" to --capable--

Col. 11, line 5, after "distal" insert --end--

Col. 12, line 15, after "distal" insert --end--

UNITED STATES PATENT AND TRADEMARK OFFICE
CERTIFICATE OF CORRECTION

PATENT NO. : 5,904,681
DATED : May 18, 1999
INVENTOR(S) : Hugh S. West, Jr.

It is certified that error appears in the above-identified patent and that said Letters Patent is hereby corrected as shown below:

Col. 12, line 18, after "distal" insert --end--

Col. 12, line 51, after "distal" insert --end--

Signed and Sealed this

Eleventh Day of January, 2000

Attest:

Q. TODD DICKINSON

*Attesting Officer*     *Acting Commissioner of Patents and Trademarks*